United States Patent
Del Seppia et al.

(10) Patent No.: US 10,525,429 B2
(45) Date of Patent: Jan. 7, 2020

(54) AMMOXIMATION REACTOR FOR CYCLOHEXANONE OXIME PRODUCTION

(75) Inventors: Alessandro Del Seppia, Porto Mantovano (IT); Elena Ghirardo, Mantova (IT)

(73) Assignee: VERSALIS S.P.A., Milanese (MI) (IT)

( * ) Notice: Subject to any disclaimer, the term of this patent is extended or adjusted under 35 U.S.C. 154(b) by 772 days.

(21) Appl. No.: 14/116,046

(22) PCT Filed: Apr. 27, 2012

(86) PCT No.: PCT/EP2012/057746
§ 371 (c)(1),
(2), (4) Date: Dec. 18, 2013

(87) PCT Pub. No.: WO2012/152600
PCT Pub. Date: Nov. 15, 2012

(65) Prior Publication Data
US 2014/0093437 A1 Apr. 3, 2014

(30) Foreign Application Priority Data
May 9, 2011 (CN) .......................... 2011 1 0209393

(51) Int. Cl.
*B01J 8/22* (2006.01)
*C07C 249/04* (2006.01)
(Continued)

(52) U.S. Cl.
CPC .............. *B01J 8/10* (2013.01); *B01J 8/006* (2013.01); *B01J 8/22* (2013.01); *B01J 8/226* (2013.01);
(Continued)

(58) Field of Classification Search
CPC ........................... C07C 249/04; C07C 249/06
See application file for complete search history.

(56) References Cited

U.S. PATENT DOCUMENTS 3,662,521 A 5/1972 Behar et al.
3,721,530 A * 3/1973 Bouchet .................. B01J 8/386
261/123
(Continued)

FOREIGN PATENT DOCUMENTS

CN 201596496 U 10/2010
CN 201988375 U 9/2011
(Continued)

OTHER PUBLICATIONS

English Machine Translation for CN 201596496 U (Oct. 2010).*

*Primary Examiner* — Jennifer A Leung
(74) *Attorney, Agent, or Firm* — Tarolli, Sundheim, Covell & Tummino LLP

(57) ABSTRACT

Ammoximation reactor for cyclohexanone oxime production comprising: (a) a reactor vessel provided with a stirrer; (b) an internal filtering system; (c) an internal liquid ammonia evaporation coil; (d) an internal gaseous ammonia toroidal distributor; (e) an external cyclohexanone toroidal distributor; (f) an internal hydrogen peroxide toroidal distributor; (g) an internal cylindrical draft tube; (h) an external cooling jacket. Said ammoximation reactor allows to obtain a better mixing of the components of the ammoximation reaction and to maximize both the heat-transfer coefficients and the mass-transfer coefficients. Moreover, said ammoximation reactor allows to increase the packing time of the catalyst used in the ammoximation reaction on the filtering system (i.e. the plugging phenomena) so as to avoid the necessity of carrying out the backwashings with nitrogen. Moreover, said ammoximation reactor does not require external downstream separation units to separate the catalyst from the reaction mixture obtained from the ammoximation reaction.

12 Claims, 1 Drawing Sheet

(51) Int. Cl.
  *B01J 8/10* (2006.01)
  *B01J 8/00* (2006.01)
(52) U.S. Cl.
  CPC ..... *C07C 249/04* (2013.01); *B01J 2208/0084* (2013.01); *B01J 2208/00867* (2013.01); *B01J 2208/00902* (2013.01); *B01J 2208/00911* (2013.01); *B01J 2208/00938* (2013.01)

(56) References Cited

U.S. PATENT DOCUMENTS

| | | | | |
|---|---|---|---|---|
| 5,324,853 | A * | 6/1994 | Jones | B01J 19/1875 560/98 |
| 6,603,027 | B1 * | 8/2003 | Catinat | B01J 37/0246 502/64 |
| 2007/0197667 | A1 * | 8/2007 | Vogel | B01D 29/33 518/700 |
| 2010/0084350 | A1 * | 4/2010 | Liu | B01J 4/004 210/767 |

FOREIGN PATENT DOCUMENTS

| | | | |
|---|---|---|---|
| EP | 0111253 A2 | 6/1984 | |
| EP | 1674449 A1 | 6/2006 | |
| GB | 577581 A | 5/1946 | |
| WO | WO 0141919 A1 * | 6/2001 | .......... B01F 3/04609 |

\* cited by examiner

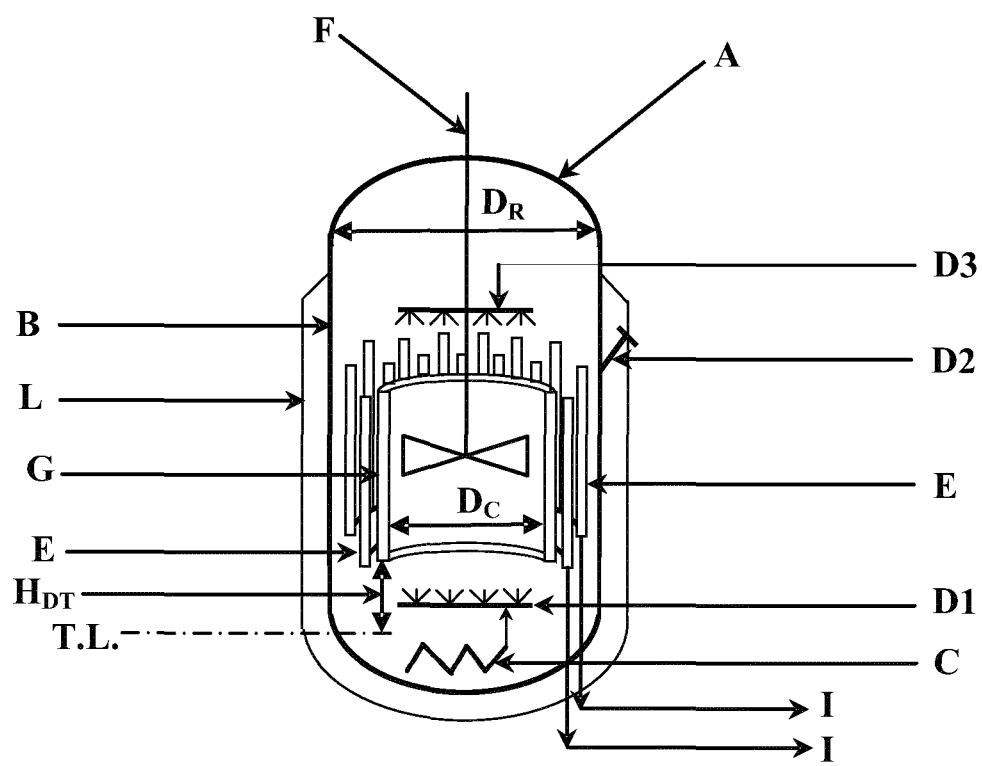

AMMOXIMATION REACTOR FOR CYCLOHEXANONE OXIME PRODUCTION

The present invention relates to an ammoximation reactor.

More in particular, the present invention relates to an ammoximation reactor for cyclohexanone oxime production comprising: (a) a reactor vessel provided with a stirrer; (b) an internal filtering system; (c) an internal liquid ammonia evaporation coil; (d) an internal gaseous ammonia toroidal distributor; (e) an external cyclohexanone toroidal distributor; (f) an internal hydrogen peroxide toroidal distributor; (g) an internal cylindrical draft tube; (h) an external cooling jacket.

Said ammoximation reactor allows to obtain a better mixing of the components of the ammoximation reaction. Furthermore, said ammoximation reactor allows to maximize both the heat-transfer coefficients and the mass-transfer coefficients. Moreover, said ammoximation reactor allows to increase the packing time of the catalyst used in the ammoximation reaction on the filtering system (i.e. the plugging phenomena) so as to avoid the necessity of carrying out the backwashings with nitrogen. Furthermore, said ammoximation reactor may be used in continuous for a long time without the necessity of stopping the cyclohexanone production in order to make external interventions (e.g., mechanical cleanings). Moreover, said ammoximation reactor does not require external downstream separation units to separate the catalyst from the reaction mixture obtained from the ammoximation reaction. Consequently, thanks to the above characteristics, said ammoximation reactor allows both to obtain a high reduction of the production costs and to maintain high productivity levels.

As it is known, cyclohexanone oxime is an important intermediate for the preparation of ε-caprolactam which is the monomer used in the production of nylon 6.

Several processes are known to produce ε-caprolactam, starting from both aromatic and non-aromatic feedstocks. In recent years, the researches are mainly focused in the development of processes for ε-caprolactam production which allow the reduction or even the elimination of the by-products formation, in particular of the ammonia-sulphate.

Conventional processes for ε-caprolactam production generally comprise four distinct steps: cyclohexanone production, hydroxylamine production, cyclohexanone oxime production from the above intermediates (i.e. cyclohexanone and hydroxylamine) and final rearrangement of the obtained cyclohexanone oxime (the so-called Beckmann rearrangement) with sulphuric acid to give ε-caprolactam.

Cyclohexanone may be produced starting from either cyclohexane (via catalytic oxidation) or phenol (via catalytic hydrogenation).

Hydroxylamine may be produced with different methods such as, for example: hydroxylamine sulphate method (HSO method or Raschig method), nitric oxide reduction method (NO method), hydroxylamine phosphate method (HPO method). However, said methods may show some drawbacks such as, for example, production of ammonia sulphate, which is a low-value by product in the case of HSO method; production of nitrogen oxide ($NO_x$) which are not only harmful, but also the main cause of environmental problems such as, for example, the greenhouse effect in the case of NO method; technical and operative difficulties in the case of HPO method.

In order to overcome the above reported drawbacks, it is known to use the photo-chemical nitrosation process which by-passes the intermediate steps of hydroxylamine preparation and allows to obtain cyclohexanone oxime directly from cyclohexane, by reaction with nitrosyl chloride and hydrogen peroxide. Said process, nothwithstanding the costs saving thanks to the elimination of process units (i.e. the elimination of the unit relative to the preparation of the hydroxylamine), requires high electric power consumptions and additional costs due to the maintenance interventions in the production equipments, in particular in the reactors, which are often necessary in order to maintain high productivity levels.

Efforts have been already made in order to overcome the above reported drawbacks.

For example, processes for producing cyclohexanone oxime comprising the ammoximation reaction of cyclohexanone with hydrogen peroxide and ammonia in the presence of titanium silicalite as a catalyst, have been disclosed in American U.S. Pat. Nos. 4,745,221, 4,794,198, 5,227,525, 5,312,987 , or in Europen Patent Application EP 1674449. Said processes do not require neutralization of sulfuric acid with ammonia which is normally required in a conventional hydroxylamine sulphate oxide method (HSO method or Raschig method) above reported, and it also has the advantage that the separation of the catalyst from the reaction mixture obtained from the ammoximation reaction is easy because it is a solid catalyst reaction process.

Moreover, besides the process costs reduction due to the elimination of the hydroxylamine formation steps, said process does not involve ammonium sulphate production, contrary to most of the other commercial technologies.

Recently, Sumitomo has commercialized a fluid-bed Beckmann rearrangement reactor that does not require the use of oleum (sulphuric acid) in the production of ε-caprolactam so avoiding the production of ammonium sulphate. The combination of the process for producing cyclohexanone oxime comprising the ammoximation reaction of cyclohexanone above disclosed with fluid-bed Beckmann rearrangement of Sumitomo, allows to eliminate the ammonium sulphate formation in the whole ε-caprolactam production process.

The ammoximation reaction above disclosed is generally carried out by feeding cyclohexanone, hydrogen peroxide and ammonia, to an ammoximation reactor, maintaining under stirring the resulting reaction mixture, operating at a temperature ranging from 50° C. to 120° C., preferably ranging from 70° C. to 100° C., at a pressure ranging from 2 barg to 4 barg, using tert-butyl alcohol (TBA) as solvent and titanium silicalite as catalyst. The ammoximation reaction is strongly exothermic and one of the most critical features in the ammoximation reactor design is the cooling system which has the function of keeping under control the reaction temperature.

Moreover, another critical point of the ammoximation reaction is the removal of the catalyst from the reaction mixture obtained from the ammoximation reaction which is normally carried out by transporting the obtained reaction mixture in an external facility as disclosed, for example, in Chinese Patent Application CN 101747228.

In order to overcome the above reported drawbacks, some efforts have been already made in the art.

For example, Chinese Utility Model CN 201596496 relates to an ammoximation reactor for the production of cyclohexanone oxime comprising a reactor body provided with a stirrer, a membrane filter installed inside the reactor body, a liquid ammonia evaporation coil at the bottom, a distributor connected to the outlet of the coil. The above reported reactor is said to avoid both the use of external membranes filters and of the backwashing system, to shorten the process, to avoid cooling reaction heat through a cooling medium, to save energy and costs.

However, studies directed to improved ammoximation reactor are still of interest.

The Applicant has faced the problem of find an improved ammoximation reactor which besides of overcoming all the drawbacks of the ammoximation reactor known in the art, allows both to obtain a high reduction of the production costs and to maintain high productivity levels.

The Applicant has found that it is possible to obtain all the above advantages by an ammoximation reactor having a specific internal design, in particular having a cylindrical draft tube inside the reactor vessel. Said ammoximation reactor allows to obtain a better mixing of the components of the ammoximation reaction. Furthermore, said ammoximation reactor allows to maximize both the heat-transfer coefficients and the mass-transfer coefficients. Moreover, said ammoximation reactor allows to increase the packing time of the catalyst used in the ammoximation reaction on the filtering system (i.e. the plugging phenomena) so as to avoid the necessity of carrying out the backwashings with nitrogen. Furthermore, said ammoximation reactor may be used in continuous for a long time without the necessity of stopping the cyclohexanone production in order to make external interventions (e.g., mechanical cleanings). Moreover, said ammoximation reactor does not require external downstream separation units to separate the catalyst from the reaction mixture obtained from the ammoximation reaction. Consequently, thanks to the above characteristics, said ammoximation reactor allows both to obtain a high reduction of the production costs and to maintain high productivity levels.

An object of the present invention therefore relates to an ammoximation reactor for cyclohexanone oxime production, comprising:
(a) a reactor vessel provided with a stirrer;
(b) an internal filtering system;
(c) an internal liquid ammonia evaporation coil installed at the bottom of the reactor vessel;
(d) an internal gaseous ammonia toroidal distributor connected to the outlet end of the evaporation coil;
(e) an external cyclohexanone toroidal distributor;
(f) an internal hydrogen peroxide toroidal distributor;
(g) an internal cylindrical draft tube;
(h) an external cooling jacket.

For the aim of the present invention and of the following claims, the definitions of the numerical ranges always comprise the extremes unless otherwise specified.

In accordance with a preferred embodiment of the present invention, said stirrer may be a high-performance stirrer.

In accordance with a preferred embodiment of the present invention, said internal filtering system comprises a set of tubular filters (candles) arranged in two concentric circular crowns, the bottoms of each tubular filter (candle) being connected together to form two continuous toroidal connecting tubes. Preferably, said tubular filters may be made of stainless steel which may be selected, for example, from the following types: AISI 316L, AISI 316, AISI 304. Preferably, the total number of said tubular filters in each continuous toroidal connecting tube may range from 30 to 80, more preferably from 40 to 70. Preferably, said tubular filters may have a filtration rating ranging from 1 µm to 10 µm. The liquid filtered reaction mixture obtained from the ammoximation reaction is collected and recovered from the outlet ends of said two continuous toroidal connecting tubes. The tubular filters are respectively connected to the reactor vessel and to the cylindrical draft tube through supports.

It has to be noted that said internal filtering system allows the obtained liquid filtered reaction mixture to leave the reactor and the catalyst used in the ammoximation reaction to remain inside, so avoiding the necessity of the external downstream separation units.

In accordance with a preferred embodiment of the present invention, said filtering system has a filtering rate (square meter of the filtering surface of the tubular filters per each cubic meter per hour of the obtained liquid filtered reaction mixture) which may range from 0.7 $(m^2 \times hour)/m^3$ to 3 $(m^2 \times hour)/m^3$, preferably from 1.5 $(m^2 \times hour)/m^3$ to 2.5 $(m^2 \times hour)/m^3$.

In accordance with a preferred embodiment of the present invention, said liquid ammonia evaporation coil may be loop-shaped, or helicoidal-shaped. Alternatively, said liquid ammonia evaporation coil may have different shapes.

In accordance with a preferred embodiment of the present invention, said gaseous ammonia toroidal distributor may be directly connected to the outlet end of the evaporation coil. Preferably, outlet holes may be evenly arranged in the bottom part of said gaseous ammonia toroidal distributor. Said gaseous ammonia toroidal distributor is connected to the reactor vessel through supports.

In accordance with a preferred embodiment of the present invention, said external toroidal cyclohexanone distributor may be endowed with circularly arranged oriented feeding nozzles.

In accordance with a preferred embodiment of the present invention, said hydrogen peroxide toroidal distributor may be endowed with holes evenly arranged in both its bottom part and its upper part. Said hydrogen peroxide toroidal distributor is connected to the reactor vessel through supports.

In accordance with a preferred embodiment of the present invention, said cylindrical draft tube may be suspended, through supports, in the centre of the reactor vessel.

In accordance with a further preferred embodiment, the ratio between the internal diameter of the cylindrical draft tube ($D_c$) and the internal diameter of said the reactor vessel ($D_r$) may range from 0.25 to 0.8, more preferably from 0.5 to 0.7.

In accordance with a further preferred embodiment, the distance ($H_{DT}$) between the bottom of the reactor vessel (T.L.) and the bottom of said cylindrical draft tube, may range from 10 mm to 800 mm, more preferably from 25 mm to 300 mm.

In accordance with a further preferred embodiment, said cylindrical draft tube allows to obtain in the reactor an outside rising velocity of the reaction mixture which may range from 0.5 m/sec to 5 m/sec, preferably from 1 m/sec to 2.5 m/sec.

It has to be noted that said outside rising velocity allows to maximize both the heat-transfer coefficients and the mass-transfer coefficients. Moreover, it has to be noted that both said outside rising velocity and said specific filtering area, allows to increase the packing time of the catalyst used in the ammoximation reaction on the filtering system (i.e. the plugging phenomena) so as to avoid the necessity of carrying out the backwashings with nitrogen. Moreover, it has to be noted that, thanks to the presence of both said outside rising velocity and said specific filtering area, said ammoximation reactor may be used in continuous for a time longer than one year without making external interventions (e.g., mechanical cleanings): consequently, the on-stream factor of said ammoximation reactor is highly increased.

In order to remove part of the reaction heat, said cylindrical draft tube may be fluxed with cooling water.

Said external cooling jacket allows to completely remove the reaction heat.

As reported above, the ammoximation reactor object of the present invention is particularly useful for cyclohexanone oxime production.

Said cyclohexanone oxime production involves an ammoximation process comprising the reaction of cyclohexanone, ammonia ($NH_3$), hydrogen peroxide ($H_2O_2$) to give cyclohexanone oxime and water, in the presence of tert-butyl alcohol (TBA) as solvent and of titanium silicalite as catalyst. The operating conditions (e.g., temperature, pressure, ect.), as well as the amounts of the different components of the ammoximation reaction, are known in the art. Further details may be found, for example, in European Patent Application EP 1674449 above cited.

In accordance with the present invention, before entering the gaseous ammonia toroidal distributor, the liquid ammonia ($NH_3$) is fed, through a pipe, to the liquid ammonia evaporation coil installed at the bottom of the reactor vessel wherein it is vaporized using part of the heat produced by the ammoximation reaction. The outlet end of said evaporation coil is directly connected to said gaseous ammonia toroidal distributor, wherein the gaseous ammonia, passing through evenly disposed holes, is injected into the reaction mixture.

The cyclohexanone is fed, tangentially, into the reactor vessel, by means of an external cyclohexanone toroidal distributor endowed with circularly arranged oriented feeding nozzles that guarantee a good mixing of the cyclohexanone into the reaction mixture. Preferably, said feeding nozzles may be present in said cyclohexanone toroidal distributor in a number ranging fro 4 to 30, more preferably from 8 to 20.

The hydrogen peroxide ($H_2O_2$) is fed, through a pipe, into the reactor vessel by means of an hydrogen peroxide toroidal distributor.

The catalyst (i.e titanium silicalite) and the tert-butyl alcohol (TBA) are also fed into the reactor vessel. The reactor vessel is charged with fresh catalyst before the start-up of the ammoximation reaction and a discontinuous make-up of fresh catalyst takes place from a dedicated catalyst feed unit. An amount of catalyst corresponding to the make-up is purged from the bottom of the reaction vessel, in a definite volume of reaction mixture, and is fed to a dedicated catalyst filtering external unit.

The liquid filtered reaction mixture obtained from the ammoximation reaction is collected and recovered from the outlet ends of said two continuous toroidal connecting tubes, as the catalyst is retained inside the reactor vessel by means of said tubular filters.

For a better understanding of the reactor object of the present invention, reference will be made to the drawing of the enclosed FIG. 1, which represents an illustrative and non-limiting embodiment.

In particular, FIG. 1 schematically represents a longitudinal section of one embodiment of the ammoximation reactor according to the present invention.

According to FIG. 1, the ammoximation reactor (A) comprises:
   a reactor vessel (B) provided with a stirrer (F);
   an internal filtering system (E) comprising a set of tubular filters (candles) arranged in two concentric circular crowns, the bottoms of each tubular filter (candle) being connected together to form two continuous toroidal connecting tubes, from the outlet ends of said two continuous toroidal connecting tubes the liquid filtered reaction mixture (I), obtained from the ammoximation reaction, is collected and recovered;
   an internal liquid ammonia evaporation coil (C) installed at the bottom of said reactor vessel (B);
   an internal gaseous ammonia toroidal distributor (D1) directly connected to the outlet end of the evaporation coil (C);
   an external cyclohexanone toroidal distributor (not represented in FIG. 1) with circularly arranged oriented feeding nozzles [(D2) represents one feeding nozzle] through which the cyclohexanone is fed to the reactor vessel (B);
   an internal hydrogen peroxide toroidal distributor (D3);
   an internal cylindrical draft tube (G);
   an external cooling jacket (L).

As reported above, in FIG. 1:
   ($D_R$) indicates the internal diameter of the reactor vessel (B);
   ($D_C$) indicates the internal diameter of the cylindrical draft tube (G);
   ($H_{DT}$) indicates the distance between the bottom (T.L.) of the reactor vessel (B) and the bottom of the cylindrical draft tube (G).

The present invention will be further illustrated below by means of a an applicative example, which is given for purely indicative purposes and without any limitation of this invention.

The analyses of cyclohexanone and of cyclohexanone oxime were carried out by using gas chromatography and, based on the analyses results, the conversion of cyclohexanone, the selectivity of cyclohexanone oxime and the yield of hydrogen peroxide, were calculated.

EXAMPLE 1

The ammoximation reactor used in the Example is as schematically show in FIG. 1.

To the reactor vessel (B) the following components were continuously fed:
   liquid ammonia ($NH_3$) (405 kg/hour) through the liquid ammonia evaporation coil (C) and the gaseous ammonia toroidal distributor (D1);
   cyclohexanone (1300 kg/hour) by means of the external cyclohexanone toroidal distributor (not represented in FIG. 1) through circularly arranged oriented feeding nozzles [(D2) represents one feeding nozzle)];
   50% w/w of an hydrogen peroxide ($H_2O_2$) aqueous solution (993 kg/hour) by means of the hydrogen peroxide toroidal distributor (D3).

The continuous ammoximation reaction was carried out, under vigorous stirring, at a temperature of 85° C., at a pressure of 2.5 barg and at a residence time ranging from 1.2 to 1.3 hours while continuosly discharging the liquid filtered reaction mixture (I), obtained from the ammoximation reaction, from the outlet ends of the two continuous toroidal connecting tubes.

The tert-butyl alcohol (TBA) was continuosly fed to the reaction vessel (B) in order to maintain its concentration equal to 55% by weight in the reaction mixture. During the ammoximation reaction, the catalyst (i.e titanium silicalite TS-1 from Polimeri Europa) was present in the reactor vessel (B), in a concentration ranging from 2% by weight to 6% by weight in the reaction mixture.

The obtained liquid filtered reaction mixture (I), continuosly discharged from the reaction vessel (B), was analyzed obtaining the following data:
   conversion of cyclohexanone: 98.5%;
   selectivity of cyclohexanone oxime: 99.4%;

yield of hydrogen peroxide on cyclohexanone oxime basis: 88.8%;
concentration of ammonia: 2%.

The data obtained shows that the ammoximation reactor according to the present invention is endowed with high productivity levels.

In order to support the high reduction of the production costs, the following tests were carried out.

The conventional ammoximation reactor needs a nitrogen backwashing every month, with a relative productivity loss equivalent to 10 hours/month.

In addition, due to the packing of the catalyst on the internal filtering system (i.e. the plugging phenomena) which increases with time, two mechanical cleanings a year (one every 6 months), are normally required for the internal filtering system, typically involving a shut-down periods of 10 days for each cleaning, with a relative productivity loss equivalent to 480 hours/year. As a result, for a conventional reactor the overall productivity loss is equivalent to 600 hours/year.

Experimental tests carried out in the ammoximation reactor as schematically show in FIG. 1, have demonstrated that the backwashing operations are completely eliminated and the ammoximation reactor was continuously run for 1 year without stopping. As a result, the total productivity loss was decreased to 240 hours/year.

The difference (Δ) between the productivity using a traditional ammoximation reactor and the productivity using the ammoximation reactor according to the present invention, was equal to 360 hours/year. Said difference (Δ), in a traditional plant for ε-caprolactam production having a nominal hourly capacity of 12.5 Mton/hours of ε-caprolactam, means a difference (Δ) in the ε-caprolactam production equal to 4500 Mton/year. Assuming for ε-caprolactam a variable cost margin of 600 $/Mton, the ammoximation reactor according to the present invention may allow to obtain a profit increase of 2.7 million $ per year compared to the conventional ammoximation reactor technology.

The invention claimed is:

1. Ammoximation reactor for cyclohexanone oxime production, comprising:
    (a) a reactor vessel provided with a stirrer;
    (b) an internal filtering system;
    (c) an internal liquid ammonia evaporation coil installed at the bottom of the reactor vessel;
    (d) an internal gaseous ammonia toroidal distributor connected to the outlet end of the evaporation coil;
    (e) an external cyclohexanone toroidal distributor;
    (f) an internal hydrogen peroxide toroidal distributor;
    (g) an internal cylindrical draft tube; and
    (h) an external cooling jacket;
    wherein said internal filtering system comprises a set of tubular filters arranged in two concentric circular crowns, the bottoms of each tubular filter being connected together to form two continuous toroidal connecting tubes, each continuous toroidal connecting tube having an outlet end to collect and recover a liquid reaction mixture obtained from an ammoximation reaction and the tubular filters retain catalyst used in the ammoximation reaction in the reactor vessel;
    wherein said external toroidal cyclohexanone distributor is endowed with circularly arranged oriented feeding nozzles for tangential feeding of cyclohexanone into the reactor vessel and mixing of the cyclohexanone with the liquid reaction mixture, and the internal toroidal hydrogen peroxide distributor feeds an aqueous hydrogen peroxide solution to the liquid reaction mixture; and wherein:
    the ratio between the internal diameter of the cylindrical draft tube ($D_C$) and the internal diameter of the reactor vessel ($D_R$) ranges from 0.25 to 0.8;
    the distance ($H_{DT}$) between the bottom of the reactor vessel (T.L.) and the bottom of the cylindrical draft tube ranges from 10 mm to 800 mm.

2. Ammoximation reactor according to claim 1, wherein said tubular filters are made of stainless steel which is selected from the following types: AISI 316L, AISI 316, and AISI 304.

3. Ammoximation reactor according to claim 1, wherein the total number of said tubular filters in each continuous toroidal connecting tube is ranging from 30 to 80.

4. Ammoximation reactor according to claim 1, wherein said tubular filters have a filtration rate ranging from 1 μm to 10 μm.

5. Ammoximation reactor according to claim 1, wherein said filtering system has a filtering rate (square meter of the filtering surface of the tubular filters per each cubic meter per hour of the obtained liquid filtered reaction mixture) which ranges from 0.7 (m²×hour)/m³ to 3 (m²×hour)/m³.

6. Ammoximation reactor according to claim 5, wherein said filtering system has a filtering rate (square meter of the filtering surface of the tubular filters per each cubic meter per hour of the obtained liquid filtered reaction mixture) which ranges from 1.5 (m²×hour)/m³ to 2.5 (m²×hour)/m³.

7. Ammoximation reactor according to claim 1, wherein said liquid ammonia evaporation coil is loop-shaped, or helicoidal-shaped.

8. Ammoximation reactor according to claim 1, wherein said gaseous ammonia toroidal distributor is directly connected to the outlet end of the evaporation coil.

9. Ammoximation reactor according to claim 1, wherein said hydrogen peroxide toroidal distributor is endowed with holes evenly arranged in both its bottom part and its upper part.

10. Ammoximation reactor according to claim 1, wherein said cylindrical draft tube is suspended, through supports, in the center of the reactor vessel.

11. Ammoximation reactor according to claim 1, wherein the ratio between the internal diameter of the cylindrical draft tube ($D_c$) and the internal diameter of the reactor vessel ($D_r$) ranges from 0.5 to 0.7.

12. Ammoximation reactor according to claim 1, wherein the distance ($H_{DT}$) between the bottom of the reactor vessel (T.L.) and the bottom of said cylindrical draft tube ranges from 25 mm to 300 mm.

* * * * *